US010688113B2

(12) United States Patent
Poras et al.

(10) Patent No.: US 10,688,113 B2
(45) Date of Patent: Jun. 23, 2020

(54) METHODS OF TREATING EYE PAIN WITH AMINOPHOSPHINIC DERIVATIVES

(71) Applicant: PHARMALEADS, Paris (FR)

(72) Inventors: Hervé Poras, Bailly (FR); Michel Wurm, Royat (FR); Stéphane Melik Parsadaniantz, Charenton le Pont (FR); Annabelle Reaux-Le Goazigo, Maison Alfort (FR)

(73) Assignee: PHARMALEADS, Paris (FR)

( * ) Notice: Subject to any disclaimer, the term of this patent is extended or adjusted under 35 U.S.C. 154(b) by 0 days.

(21) Appl. No.: 16/272,573

(22) Filed: Feb. 11, 2019

(65) Prior Publication Data

US 2019/0167701 A1 Jun. 6, 2019

Related U.S. Application Data

(63) Continuation of application No. 15/779,220, filed as application No. PCT/EP2016/079285 on Nov. 30, 2016, now abandoned.

(30) Foreign Application Priority Data

Nov. 30, 2015 (FR) ..................................... 15 61598

(51) Int. Cl.
| | | |
|---|---|---|
| *A61K 31/662* | (2006.01) | |
| *A61P 27/02* | (2006.01) | |
| *A61K 9/00* | (2006.01) | |
| *A61K 9/08* | (2006.01) | |
| *A61K 47/40* | (2006.01) | |

(52) U.S. Cl.
CPC .......... *A61K 31/662* (2013.01); *A61K 9/0048* (2013.01); *A61K 9/08* (2013.01); *A61K 47/40* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 8,703,747 | B2 | 4/2014 | Roques et al. |
| 10,131,681 | B2 | 11/2018 | Roques et al. |

FOREIGN PATENT DOCUMENTS

| | | | |
|---|---|---|---|
| FR | 2755135 A1 | 4/1998 | |
| FR | 2934627 A1 | 2/2010 | |
| WO | WO-9818803 A1 | 5/1998 | |
| WO | WO-2010010106 A1 | 1/2010 | |

OTHER PUBLICATIONS

International Search Report (English and French) and Written Opinion of the ISA for PCT/EP2016/079285; ISA/EP. Rijswijk, NL, dated Feb. 24, 2017.

Anonymous, "Pharmaleads announces promising phase 1 result of PL-37," Nov. 29, 2011, retrieved from Internet Thompson Reuters Integrity Drug News.
Belluzi et al., "Analgesia induced in vivo by central administration of enkephalin in rat," Nature, vol. 260, pp. 625-626, Apr. 15, 1976.
Belmonte et al., "Neural basis of sensation in intact and injured corneas," Exp. Eye Research, vol. 78 (2004), pp. 513-525.
Bonnard et al., "Long-lasting oral analgesis effects of N-protected aminophosphinic dual ENKephalinase inhibitors (DENKIs) in peripherally controlled pain," Pharmacol. Research & Perspectives, vol. 3, Issue 2, 2015, pp. 1-15.
Bourgoin et al., "Effects of Kelatorphan and Other Peptidase Inhibitors on the In Vitro and In Vivo Release of Methionine-Enkephalin-Like Material From the Rat Spinal Cord," Journal of Pharm. Exp. Ther., vol. 238, (1986), pp. 360-366.
Chen, et al., "Long Lasting Antinociceptive Properties of Enkephalin Degrading Enzyme (NEP and APN) Inhibitor Prodrugs," J. Med. Chem. vol. 44 (2001), pp. 3523-3530.
Chen, et al., "Phosphinic Derivatives as New Dual Enkephalin-Degrading Enzyme Inhibitors: Synthesis, Biological Properties, and Antinociceptive Activities," J. Med. Chem., vol. 43 (2000), pp. 1398-1408.
Friedman, "Impact of dry eye disease and treatment on quality of life," Current Opin. Ophthalmology, 2010, vol. 21, No. 4, pp. 310-316.
Gonzalez et al., "Reduction of Capsaicin-Induced Ocular Pain and Neurogenic Inflammation by Calcium Antagonists," Investigative Ophthalmology Visual Science, Nov. 1993, vol. 34, No. 12, pp. 3329-3335.
Hugues et al, "Identification of two related pentapeptides from the brain with potent opiate agonist activity," Nature, vol. 258, Dec. 18, 1975, pp. 577-580.
Jutkiewicz et al., "RB101-mediated Protection of Endogenous Opioids: Potential Therapeutic Utility?" CNS Drugs Reviews, vol. 13, No. 2 (2007), pp. 192-205.
Khatri et al., "Regulation of Endotoxin-Induced Keratitis by PECAM-1, MIP-2 and Toll-like Receptor 4," Invest. Ophthal. Visual Science, (2002), 43, pp. 2278-2284.
Launay et al., "Ocular inflammation induces trigeminal pain, peripheral and central neuroinflammatory mechanisms," Neurobiol. Disease. 88 (2016), pp. 16-28.
Le Guen et al., "Pain management by a new series of dual inhibitors of enkephalin degrading enzymes: long lasting antinociceptive properties and potentiation by $CCK_2$ antagonist or methadone," Pain, vol. 104 (2003), pp. 139-148.
Lord et al., "Endogenous opioid peptides: multiple agonists and receptors," Nature, vol. 267, Jun. 9, 1977, pp. 495-499.
Malfroy et al., "High-affinity enkephalin-degrading peptidase in brain is increased after morphine," Nature, vol. 276, pp. 523-526, Nov. 30, 1978.
Pflugfelder, "Prevalence, Burden, and Pharmacoeconomics of Dry Eye Disease," Amer. J. Managed Care, Apr. 2008, vol. 14 (3 Suppl.), pp. S102-S106.
Roques, "Novel approaches to targeting neuropeptide systems," Trends Pharmacol. Sci., vol. 21 (2000), pp. 475-483.
Roques et al., "Inhibiting the breakdown of endogenous opioids and cannabinoids to alleviate pain," Nature Review Drug Discovery, vol. 11, Apr. 2012 (Apr. 2012), pp. 292-310.

(Continued)

*Primary Examiner* — Alicia L Otton
(74) *Attorney, Agent, or Firm* — Harness, Dickey & Pierce, P.L.C.

(57) ABSTRACT

The disclosure relates to a method of treating or preventing eye pain in a subject in need thereof. The method includes administering a compound of formula (I), $R_1$—NH—CH$(R_2)$—P(=O)(OH)—CH$_2$—C($R_3$)($R_4$)—CONH—C($R_5$)$(R_6)$—COOR$_7$, to the subject.

20 Claims, 4 Drawing Sheets

(56) References Cited

OTHER PUBLICATIONS

Roques et al., "Neutral Endopeptidase 24.11: Structure, Inhibition, and Experimental and Clinical Pharmacology," Pharmacology Rev., vol. 45, (1993), pp. 87-146.
Rosenthal & Borsook, "The Corneal Pain System. Part I: The Missing Piece of the Dry Eye Puzzle," The Ocular Surface, Jan. 2012, vol. 10 No. 1, pp. 2-14.
Rosenthal et al., "Corneal Pain without Stain: Is it Real?" The Ocular Surface, Jan. 2009, vol. 7, No. 1, pp. 28-40.
Stiles et al., "Effect of topical administration of 1% morphine sulfate solution on signs of pain and corneal wound healing in dogs," American Journal of Veterinary Res., vol. 64, No. 7, Jul. 2003.
Waksman et al., "Autoradiographic comparison of the distribution of the neutral endopeptidase 'enkephalinase' and of μ and δ opioid receptors in rat brain," Proc. Natl. Acad. Sci. USA, vol. 83, pp. 1523-1527, Mar. 1986.
Waksman et al., "In Vitro and In Vivo Effects of Kelatorphan on Enkephalin Metabolism in Rodent Brain," Eur. J. Pharmacol., vol. 117 (1985), pp. 233-243.
Wenk, et al., "Effect of morphine sulphate eye drops on hyperalgesia in the rat cornea," Pain, vol. 105, 2003, pp. 455-465.
Yawn, et al., "Herpes Zoster Eye Complications: Rates and Trends," Mayo Clinic Proc., vol. 88, No. 6, Jun. 2013, pp. 562-570.
Zhang et al., "Sensory Neural Mechanisms in Contraction of the Rabbit Isolated Sphincter Pupillae: Analysis of the Responses to Capsaicin and Electrical Field Stimulation," Exp. Eye Res. (1984), vol. 38, pp. 153-163.

Von Frey Filaments D5

METHODS OF TREATING EYE PAIN WITH AMINOPHOSPHINIC DERIVATIVES

CROSS-REFERENCE TO RELATED APPLICATIONS

This application is a continuation of U.S. patent application Ser. No. 15/779,220, filed on May 25, 2018, which is a National Phase Entry of International Patent Application No. PCT/EP2016/079285, filed on Nov. 30, 2016, which claims priority to French Patent Application No. 1561598, filed on Nov. 30, 2015. The entire disclosures of each of the above applications are incorporated herein by reference.

BACKGROUND AND SUMMARY

The present invention relates to the prevention and treatment of eye pain.

Pain is a nociceptive response to local stimulation in the body. Pain perception in the central nervous system requires the transmission of pain stimuli by the peripheral nerve fibres. When tissue is stimulated, whether thermally, mechanically or chemically, electrochemical signals are transmitted from the sensory nerve endings towards the spinal column, and from there towards the brain where pain is felt.

There are various kinds of pain, of highly diverse origins, the treatment of which is radically different depending on the type of pain and its aetiology. Eye pain is a particular form of pain which appears under many conditions, for instance accidental trauma, surgical procedures, uveitis, dry eye syndrome and diabetic neuropathies.

The medicinal products commonly used to treat eye pain are topical or systemic nonsteroidal anti-inflammatories, systemic analgesics, local anaesthetics and, in extreme cases, systemic opiates. These treatments have limited efficacy and systemic local side effects. Local anaesthetics act on pain by directly inhibiting nerve transmission. Their use is limited to brief administration under medical supervision because their mechanism of action induces inhibitory effects at the cellular level in fibroblasts or the surrounding neuronal cells. That is why, even if the pain sensation can be alleviated by local anaesthetics, tissue healing and physiology can be impaired. It is thus important to discover other analgesic agents, without anaesthetic activity, which are effective and well-tolerated when applied topically to the painful eye.

Opiates such as morphine sulphate are used systemically to treat severe eye pain, but they have many adverse effects, such as sedation, nausea, constipation and respiratory depression, which substantially limit their use, particularly for chronic eye pain. It has been shown that topical administration of morphine relieves pain associated with corneal lesions in dogs (Stiles et al. (2003) *Am. J. Vet. Res.*, 64, 813-818) and in rats (Wenk et al. (2003) *Pain*, 105, 455-465) without retarding healing of the corneal wound (Stiles et al. (2003) *Am. J. Vet. Res.*, 64, 813-818).

Perception, transmission and regulation of nociceptive inputs are subordinate to several neurotransmitters, in particular the enkephalins (Met-enkephalin and Leu-enkephalin). The latter are pentapeptides, endogenous opioids, first discovered in the mammalian brain (Hugues et al. (1975) *Nature*, 258, 577-580). They bind mainly to two receptor classes, μ- and δ-opioid receptors (Lord et al. (1977) *Nature*, 267, 495-499), which have different functions and distributions (Waksman et al. (1986) *Proc. Natl. Acad. Sci.*, 83, 1523-1527).

The antinociceptive properties of the enkephalins have been shown after intracerebroventricular administration of exogenous enkephalins (Belluzi et al. (1976) *Nature*, 260, 625-626). However, this response is highly transient because these peptides are metabolized very rapidly by enzymes. Synthetic enkephalin analogues, modified to make them resistant to enzymatic degradation, have shown antinociceptive properties equal to those of morphine, but have also exhibited the same adverse side effects as morphine.

Furthermore, it is known that the enkephalins (Tyr-Gly-Gly-Phe-Met and Tyr-Gly-Gly-Phe-Leu) are physiologically inactivated by two zinc metallopeptidases, neprilysin (EC 3.4.24.11, NEP), which cleaves the $Gly^3$-$Phe^4$ bond (Malfroy et al. (1978) *Nature*, 276, 523-526), and aminopeptidase N (EC 3.4.11.2, APN), which cleaves the $Tyr^1$-$Gly^2$ bond of these peptides. (Waksman et al. (1985) *Eur. J. Pharmacol.*, 117, 233-243; reviewed in Roques et al. (1993) *Pharmacol. Rev.*, 45, 87-146). Inhibiting these two enzymatic activities by fully protecting enkephalins (Bourgoin et al. (1986) *J. Pharm. Exp. Ther.*, 238, 360-366), reveals the pharmacological activities, particularly the analgesic and antidepressant activities (Roques (2000) *Trends Pharmacol. Sci.*, 21, 475-483; Jutkiewicz et al. (2007) *CNS Drugs Reviews*, 13, 192-205), of these endogenous opioids, the enkephalins.

Aminophosphinic derivatives, "true" mixed inhibitors, i.e., inhibiting both APN and NEP, have been described in previous patents and publications (WO9818803; WO2010010106; Chen et al. (2000) *J. Med. Chem.*, 43, 1398-1408; Chen et al. (2001) *J. Med. Chem.*, 44, 3523-3530; Le Guen et al. (2003) *Pain*, 104, 139-148; Bonnard et al. (2015) *Pharmacol. Res. Persp.*, 3(2), e00116, doi: 10.1002/prp2.116). Good antinociceptive activity, with a long duration of action, has been shown on numerous animal models of nociception after oral and/or iv administration (Chen et al. (2000) *J. Med. Chem.*, 43, 1398-1408; Chen et al. (2001) *J. Med. Chem.*, 44, 3523-3530; Le Guen et al. (2003) *Pain*, 104, 139-148; Bonnard et al. (2015) *Pharmacol. Res. Persp.*, 3(2), e00116, doi: 10.1002/prp2.116).

The use of said compounds as topical ocular analgesics has never been disclosed or suggested. It has also never been shown that prodrugs of mixed inhibitors of NEP and APN could hydrolyse to give a compound capable of reaching its target, thus allowing a long-lasting analgesic response. One of the objects of this invention is thus to provide novel aminophosphinic-type compounds capable of inhibiting both of the enzymatic activities (neprilysin and aminopeptidase N) responsible for the degradation of enkephalins, the latter which can have action within the context of eye pain.

More particularly, the invention relates to compounds having the formula (I):

$$R_1\text{—NH—CH}(R_2)\text{—P(=O)(OH)—CH}_2\text{—C}(R_3)$$
$$(R_4)\text{—CONH—C}(R_5)(R_6)\text{—COOR}_7 \quad\quad (I)$$

Wherein:

$R_1$ is
 a hydrogen
 an (acyloxy)alkyl carbamate group —C(=O)—O—C(R)(R')—OC(=O)—R" wherein R and R' are each independently a hydrogen, an alkyl group and R" is an alkyl group.

$R_2$ is:
 a linear or branched, saturated or unsaturated hydrocarbon chain having from 1 to 6 carbon atoms $R_3$ and $R_4$ are each independently:
 a hydrogen
 a phenyl or benzyl group, optionally substituted on the phenyl ring by:

1 to 5 halogen atoms, particularly fluorine or bromine.

an OH, SH, OR" or SR" radical, R" having the same definition as above.

an amino group optionally mono- or di-substituted by a cyclic or linear aliphatic group having from 1 to 6 carbon atoms.

a trifluoromethyl group an aromatic or heteroaromatic group having 5 or 6 atoms a heteroaromatic group having 5 or 6 atoms, containing 1 or 2 heteroatom(s) selected from oxygen, nitrogen or sulphur, wherein the sulphur and nitrogen atoms may be oxidized in S-oxide or N-oxide form.

a methylene substituted by an aromatic or saturated heterocycle having 5 or 6 atoms, the heteroatom being an oxygen, a nitrogen or a sulphur, wherein the nitrogen and sulphur atoms may be oxidized in N-oxide or S-oxide form $R_3$ and $R_4$ are not simultaneously a hydrogen atom.

$R_5$ and $R_6$ are each independently a hydrogen atom a linear or branched, saturated or unsaturated hydrocarbon chain having from 1 to 6 carbon atoms $R_7$ is a hydrogen a $CH_2COOR'''$ or $CH(CH_3)COOR'''$ radical, R''' being a saturated hydrocarbon chain having from 1 to 6 carbon atoms, optionally substituted by a $C_1$ to $C_3$ alkoxy group, a $C_5$ to $C_8$ cycloalkyl group a heteroaromatic phenyl, benzyl or alkyl group.

a CH(R)O—C(O)OR' or CH(R)OC(O)R' group wherein R and R' have the same definitions as above;

or a pharmaceutically acceptable salt of said compounds for use in the treatment and/or prevention of eye pain.

The compounds of the invention can advantageously be used to prevent or relieve eye pain, in particular dry eye syndrome. The compounds of the invention can advantageously be used to prevent or treat corneal neuropathic pain, in particular neuropathic hyperalgesia.

DETAILED DESCRIPTION

Eye Pain

Neuropathic pain has peripheral and central causes and can specifically affect the cornea of the eye. There are many causes of neuropathies, but all originate in damaged or deteriorated nerve fibres resulting from surgical incisions, trauma, viruses (zoster), metabolic disorders (diabetes), neurotoxic medicinal products or chronic inflammation. Current medicinal products have little efficacy, which makes the discovery and development of novel compounds essential.

Corneal neuropathic hyperalgesia involves a dysfunctional corneal pain perception and control system. It is associated with significant discomfort and persistent heightened corneal sensitivity (peripheral sensitization) in the absence of overt trauma or harmful stimuli (reviewed in Belmonte et al. (2004) *Exp. Eye Res.*, 78(3), 513-525; Rosenthal & Borsook (2012) *Ocul. Surf.*, 10(1), 2-14; Rosenthal et al. (2009) *Ocul. Surf.*, 7(1), 28-40).

Continuous excitation of corneal nerves resulting from corneal lesions or irritation releases neuropeptides and mediators of inflammation which increase the inflammatory reaction (neurogenic inflammation), thus leading to hyperalgesia. Corneal hypersensitivity, neuroinflammation, pain and photophobia are reported among patients after eye surgery or chemical or toxic exposure, including repeated use of benzalkonium chloride, the usual preservative in eye drops. Corneal neuropathic pain is also a consequence of eye conditions generally referred to as dry eye syndrome. That includes non-infectious immunological causes such as Goujerot-Sjögren syndrome or systemic lupus as well as ophthalmic zoster due to Herpesvirus zoster (reviewed in Rosenthal & Borsook (2012) *Ocul. Surf.*, 10(1), 2-14; Yawn et al. (2013) *Mayo Clin. Proc.*, 88(6), 562-570). Up to 20% of adults aged 45 years older are affected by dry eye syndrome, which represents a major health issue with substantial economic and social consequences (reviewed in Friedman (2010) *Curr. Opin. Ophthalmol.*, 21(4), 310-316; Pfugfelder (2008) *J. Manag. Care,* 14 (3 Suppl), S102-S106).

In a great many cases, dry eye syndrome is refractory to treatment and there is no real correlation between the symptoms and associated signs. For example, whereas inflammatory corneal hyperalgesia, due to desiccation of the ocular surface (dry eye evaporation), is the most common form of corneal neuropathic hyperalgesia, many patients presenting with symptoms of ocular dryness do not have objective signs of dry eye (reduced lachrymal volume) or of superficial corneal erosion. Moreover, neuropathy can sometimes precede deterioration of the lachrymal film (Rosenthal & Borsook (2012) *Ocul. Surf.*, 10(1), 2-14; Rosenthal et al. (2009), *Ocul. Surf.*, 7(1), 28-40).

The compounds prescribed for corneal neuropathic pain include a wide variety of different compounds such as opiates, nonsteroidal anti-inflammatories, sodium channel blockers (local anaesthetics), antiepileptics, tricyclic antidepressants and GABA analogues. This arsenal remains inadequate, however, and the complex nature of neuropathic corneal pain is shown by the fact that there is no known single treatment effective against the various symptoms. Furthermore, the side effects of many currently prescribed agents limit the therapeutic window. Corneal inflammatory neuropathic pain thus represents an unmet therapeutic need (Rosenthal & Borsook (2012) *Ocul. Surf.*, 10(1), 2-14; Rosenthal et al. (2009) *Ocul. Surf.*, 7(1), 28-40).

Compounds of the Invention:

In the present invention, the term "pharmaceutically acceptable" refers to that which is useful in the preparation of a pharmaceutical composition which is generally safe, non-toxic and neither biologically nor otherwise undesirable and which is acceptable for both veterinary and human pharmaceutical use.

The term "pharmaceutically acceptable salts" of a compound, as used in the present invention, refers to salts which are pharmaceutically acceptable, as defined herein, and which have the desired pharmacological activity of the parent compound. Within the context of the present invention, they are addition salts obtained with an inorganic or organic base. Thus, the salt formed corresponds:

either to the replacement of an acidic proton by a metal ion, for example an alkaline metal ion ($Na^+$, $K^+$ or $Li^+$, for example), an alkaline-earth metal ion (like $Ca^{2+}$ or $Mg^{2+}$) or an aluminium ion,
or to the coordination of said acidic proton with an organic or inorganic base.

Acceptable organic bases include amines such as ammonia, diethanolamine, ethanolamine, N-methylglucamine, triethanolamine, triethylamine, tromethamine and the like. Acceptable inorganic bases include aluminium hydroxide, calcium hydroxide, lithium hydroxide (lithine), potassium hydroxide (potash), sodium carbonate and sodium hydroxide (soda). Advantageously, the pharmaceutically acceptable salts of the compounds of the invention will be addition salts obtained with a pharmaceutically acceptable inorganic or organic base, such as lithine, soda, potash, ammonia, a tertiary amine of formula $NR_aR_bR_c$, where $R_a$, $R_b$ and $R_c$ are each independently an alkyl group as defined below, such as triethylamine, or a basic amino acid such as lysin or arginine and derivatives thereof.

The term "unsaturated", as used in the present invention, means that the hydrocarbon chain includes one or more unsaturation(s). The term "unsaturation", as used in the present invention, refers to a double or triple bond.

The term "halogen atom", as used in the present invention, refers to a fluorine, chlorine, bromine or iodine atom. Advantageously, it is a fluorine, chlorine or bromine atom. More advantageously, it is a fluorine or bromine atom, preferably fluorine.

The term "amino" group, as used in the present invention, refers to a group having the formula —NR*R**, where R* and R** are each independently a hydrogen atom or a linear, branched or cyclic, saturated or unsaturated hydrocarbon group having from 1 to 6, preferably from 1 to 4, carbon atoms, or R* and R** form, together with the nitrogen atom to which they are attached, a 5- or 6-member heterocycle which is optionally saturated and which does not contain a heteroatom other than the nitrogen to which the two radicals R* and R** are attached. In particular, the amino group can be an —$NH_2$, —NHMe, —NHEt, —NHPr, —NHiPr, —NHBu, —NHiBu, —NHtBu, piperidinyl or pyrrolidinyl group.

The term "aromatic" group, as used in the present invention, refers to an aromatic group having preferably from 5 to 10 carbon atoms, unless specified otherwise, and having one or more fused rings, such as for example a phenyl or naphthyl group. Advantageously, it is phenyl.

The term "heteroaromatic" group, as used in the present invention, refers to any aromatic group as defined above in which one or more carbon atom(s) has(have) been replaced by one or more heteroatom(s), advantageously 1 to 4, even more advantageously 1 to 2, such as for example sulphur, nitrogen or oxygen atoms, wherein the nitrogen and sulphur atoms can be optionally oxidized in S-oxide or N-oxide form. Exemplary heteroaromatic groups include furyl, thienyl, pyrrolyl, pyridinyl, pyrimidyl, pyrazolyl, imidazolyl, tetrazolyl and indyl groups.

The term "heteroaromatic ring having 5 or 6 atoms", as used in the present invention, refers to a heteroaromatic group as defined above having only one 5- or 6-atom ring. It is in particular a thienyl, pyrrolyl, pyridinyl, pyrimidyl, pyrazolyl, imidazolyl or tetrazolyl group.

The term "heterocycle", as used in the present invention, refers to a hydrocarbon ring, advantageously having 5 or 6 atoms, of which one or more carbon atom(s) has(have) been replaced by one or more heteroatom(s), advantageously 1 to 4, even more advantageously 1 to 2, such as for example sulphur, nitrogen or oxygen atoms, wherein the sulphur and nitrogen atoms can be optionally oxidized in N-oxide or S-oxide form. Unless specified otherwise, this ring may be saturated or aromatic. If the heteroatom(s) is(are) selected from nitrogen and sulphur, the heterocycle may be in particular one of the following groups: piperidinyl, pyrrolidinyl, pyrrolyl, thienyl, pyrazolyl, imidazolyl, pyridinyl, pyridazinyl, pyrimidinyl, piperazinyl, thiadiazolyl, tetrahydrothienyl or thiazolyl.

The term "alkyl", as used in the present invention, refers to a saturated, linear or branched hydrocarbon chain having from 1 to 4 carbon atoms, unless specified otherwise. It is in particular methyl, ethyl, n-propyl, isopropyl, n-butyl, isobutyl, sec-butyl, tert-butyl, n-pentyl, n-hexyl groups.

The term "cycloalkyl", as used in the present invention, refers to a saturated hydrocarbon ring having from 5 to 8 carbon atoms, in particular a cyclohexyl, cyclopentyl or cycloheptyl group.

The term "alkylheteroaromatic", as used in the present invention, refers to a heteroaromatic group as defined above attached to the molecule via an alkyl group as defined above. It is in particular a thenylmethyl or furylmethyl group.

In a first variant, $R_1$ is an (acyloxy)alkyl carbamate group —C(=O)—O—C(R)(R')—OC(=O)—R". In particular, $R_1$ is a —C(=O)—O—CHMe—OC(=O)—$CHMe_2$ group. In a second variant, $R_1$ is a hydrogen atom. Also advantageously, radical $R_2$ is a saturated, linear or branched hydrocarbon chain having from 1 to 4 carbon atoms. Preferably, radical $R_2$ is a methyl group.

According to an advantageous variant of the invention, $R_3$ is a hydrogen atom and $R_4$ is as previously defined. Advantageously, $R_3$ is a hydrogen atom and $R_4$ is a benzyl group optionally substituted by 1 to 5 halogen atom(s) such as fluorine or bromine, a phenyl or a 5- or 6-member heteroaromatic group. In particular, $R_3$ is a hydrogen atom and $R_4$ is a benzyl group substituted in the para position by a halogen atom, such as a bromine atom, or by a phenyl.

Also advantageously, radical $R_5$ is a hydrogen atom. Also advantageously, radical $R_6$ is an alkyl group such as a methyl group. Also advantageously, radical $R_7$ is a hydrogen atom or a benzyl.

According to an advantageous variant of the invention, the radicals are defined as follows:
$R_1$ is a —C(=O)—O—C(R)(R')—OC(=O)—R" group wherein R is a hydrogen atom and R' and R" are an alkyl group;
$R_2$ is an alkyl group,
$R_3$ is a hydrogen atom;
$R_4$ is a benzyl group substituted at the para position by a halogen atom (bromine) or by a phenyl;
$R_5$ is a hydrogen atom;
$R_6$ is an alkyl group;
$R_7$ is a hydrogen atom.

According to a particular embodiment, the compound of the invention is selected from the following compounds:
2-(2-Biphenyl-4-ylmethyl-3-{hydroxy-[1-(1-isobutyryloxyethoxycarbonylamino)-ethyl]-phosphinoyl}-propionylamino)-propionic acid benzyl ester
2-(2-Biphenyl-4-ylmethyl-3-{hydroxy-[1-(1-isobutyryloxyethoxycarbonylamino)-ethyl]-phosphinoyl}-propionylamino)-propionic acid
2-(2-Biphenyl-4-ylmethyl-3-{hydroxy-[1-(1-isobutyryloxyethoxycarbonylamino)-ethyl]-phosphinoyl}-propionylamino)-propionic acid ethyl ester
2-(2-Biphenyl-4-ylmethyl-3-{hydroxy-[1-(1-isobutyryloxyethoxycarbonylamino)-ethyl]-phosphinoyl}-propionylamino)-propionic acid ethoxycarbonyloxy ester 2-(2-(4-Bromo-benzyl)-3-{hydroxy-[1-(1-isobutyryloxy-ethoxycarbonylamino)-ethyl]-phosphinoyl}-propionylamino)-propionic acid benzyl ester 2-(2-(4-Bromo-benzyl)-3-{hydroxy-[1-(1-isobutyryloxy-ethoxycarbonylamino)-ethyl]-phosphinoyl}-propionylamino)-propionic acid 2-(2-Biphenyl-4-ylmethyl-3-{hydroxy-[1-(amino)-ethyl]-phosphinoyl}-propionylamino)-propionic acid benzyl ester 2-(2-Biphenyl-4-ylmethyl-3-{hydroxy-[1-(amino)-ethyl]-phosphinoyl}-propionylamino)-propionic acid 2-(2-Biphenyl-4-ylmethyl-3-{hydroxy-[1-(1 amino)-ethyl]-phosphinoyl}-propionylamino)-propionic acid ethyl ester 2-(2-Biphenyl-4-ylmethyl-3-{hydroxy-[1-(amino)-ethyl]-phosphinoyl}-propionylamino)-propionic acid ethoxycarbonyloxy ester 2-(2-(4-Bromo-benzyl)-3-{hydroxy-[1-(amino)-ethyl]-phosphinoyl}-propionylamino)-propionic acid benzyl ester 2-(2-(4-Bromo-benzyl)-3-{hydroxy-[1-(amino)-ethyl]-phosphinoyl}-propionylamino)-propionic acid 2-(2-(4-Bromo-benzyl)-3-{hydroxy-[1-(amino)-ethyl]-phosphinoyl}-propionylamino)-propionic acid ethyl ester.

The compounds of formula (I) have been described as dual inhibitors of APN and NEP and exhibit analgesic activities in numerous models of central or peripheral pain after intravenous or oral administration (Chen et al. (2000) *J. Med. Chem.*, 43, 1398-1408; Bonnard et al. (2015) *Pharmacol. Res. Persp.*, 3(2), e00116, doi: 10.1002/prp2.116). The compounds of formula (I) can be synthesized, for example, by methods described in: FR 2 755 135 and FR 2 934 267. Compound 1, for example, can be synthesized as described in Chen et al. (2000) *J. Med. Chem.*, 43, 1398-1408 and compound 2, for example, can be synthesized as described in Bonnard et al. (2015) *Pharmacol. Res. Persp.*, 3(2), e00116, doi: 10.1002/prp2.116.

The compounds of formula (I) are formulated according to the methods described by the person skilled in the art, in particular for the desired route of administration. In particular, the compounds are formulated as an ophthalmic composition, in particular as eye drops, ophthalmic ointments, ophthalmic gels, or ophthalmic inserts.

Preferentially, the administered compositions of the present invention will be formulated as solutions, suspensions or other dosage forms for topical administration, in particular ocular administration. Consequently, such compositions are formulated so as to be well-tolerated (in particular acceptable pH) and to have physiological osmolarity. It is also preferable that the compositions are sterile and formulated so as to avoid bacterial contamination during use. Ophthalmic solutions are advantageously clear, characterized by an absence of particles. Suspensions are advantageously characterized by a particle size of less than 25 µm. By way of example, pharmaceutical formulations for ocular administration include:

Eye drops: in the form of sterile solutions, suspensions or emulsions containing one or more active principles. Aqueous or water-soluble solvents or solvent mixtures are preferred. Eye drops can be packaged in single- or multiple-dose packaging.

Ophthalmic ointments, i.e., sterile, semi-solid preparations for application to the conjunctiva, containing one or more active principles and suitable excipients (petroleum jelly, liquid paraffin).

Ophthalmic gels, i.e., sterile, semi-solid preparations for application to the conjunctiva, containing one or more active principles and suitable excipients. The excipient is advantageously a hydrophilic polymer that forms a gel in the presence of water (carbomer, Carbopol®, polyacrylic acid).

Ophthalmic inserts, i.e., sterile, solid or semi-solid preparations for insertion in the conjunctival sac. They generally consist of a reservoir of active principle embedded in a matrix surrounded by a membrane for controlling release. The active principle is gradually released.

Aqueous solutions will preferably be used because they are easier to formulate, and it is also easier for a patient to administer such a composition by instilling 1 or 2 drops of the solution in the affected eye. All the same, the composition may also be a suspension, a viscous or semi-viscous gel, or other types of solid or semi-solid compositions.

The vehicle preferably used for the ophthalmic formulations of the present invention is Milli-Q water, and preferentially physiological saline solution. In order to avoid pH drift during storage, the pH of such a solution will preferably be kept between 5.5 and 8, and preferentially between 6.5 and 7.2, with suitable buffer such as acetate, citrate, phosphate or borates buffers. The formulations may also contain conventional, pharmaceutically acceptable preservatives, stabilizers and/or penetration enhancers. Thus, the ophthalmic composition is advantageously an aqueous solution, advantageously having a pH in the range from 5.5 to 8.

The compositions administered in accordance with the methods described in the present invention contain an active amount for ophthalmic use of a compound of formula (I). That means a sufficient amount to prevent or relieve eye pain. Generally, the compositions described in the present invention will contain from 0.01% to 3% (weight/volume) of a compound of formula (I). Preferably, the compositions of the present invention will contain from 0.1% to 1% (weight/volume) of a compound of formula (I). Thus, the ophthalmic composition advantageously comprises from 0.01% to 3% (weight/volume) of said compound of formula (I), more advantageously from 0.1% to 1% (weight/volume). The administered composition may also contain other various ingredients which include, but are not limited to, surfactants, osmolarity agents, buffers, preservatives, co-solvents, or viscosity enhancers.

Various osmolarity adjusters can be used to adjust the osmolarity of a solution in order to make the composition more like natural tears. For example, sodium chloride, potassium chloride, magnesium chloride, calcium chloride, dextrose and/or mannitol can be used in order to approach physiological osmolarity (generally, about 150-450 mOsm and preferentially 250-350 mOsm).

The preservatives which can be used in the ophthalmic formulations of the present invention include, but are not limited to, benzalkonium chloride, chlorobutanol, benzododecinium bromide, methyl paraben, propyl paraben, thimerosal, phenylmercuric acetate and phenylmercuric nitrate. Such preservatives are generally used in an amount from 0.001% to 1.0% weight/volume. The viscosity agents which can be used in the ophthalmic formulations of the present invention include, but are not limited to, monomeric polyols, povidone, hydroxypropylmethyl cellulose, poloxamers, carboxymethyl cellulose, carbomers or hydroxyethylcellulose, dextrans such as dextran 70, water-soluble proteins such as gelatin, etc. The penetration agents which can be used include organic solvents such as dimethylsulphoxide or other sulphoxides, dimethylacetamide and pyrrolidones; certain amide of heterocyclic amine compounds, glycols (e.g., propyleneglycol); propylene carbonates; oleic acid; alkylated amines and other ammonium salt derivatives; various anionic, cationic or non-ionic surfactants, etc.

In a preferred embodiment, a formulation of the present invention comprises a cyclodextrin, such as hydroxypropyl beta-cyclodextrin or sulphobutyl ether beta-cyclodextrin, or sodium polystyrene sulphonate. Thus, the ophthalmic composition advantageously further comprises cyclodextrin, such as hydroxypropyl beta-cyclodextrin or sulphobutyl ether beta-cyclodextrin, or sodium polystyrene sulphonate.

Example of Pharmacological Activity (a) Capsaicin Test

In order to study the pharmacological activity of the present invention in the case of ocular pain, the compounds of formula (I) were tested using the model of capsaicin-induced ocular pain. In this model, previously used in the literature (Gonzalez et al. (1993) *Invest. Ophthalmol. Vis. Sci.*, 34(12), 3329-3335), in adult rabbits, the number of lid-squeezing movements, the degree of palpebral opening, miotic response and conjunctival vasodilation evoked by a bilateral instillation of 30 μL of capsaicin (33 mM) were measured at different times after administration of the drug. To that end, the responses to this test in eyes pre-treated with various calcium antagonists (diltiazem, verapamil or nifedipine) were compared with those that had received only vehicle. For example, diltiazem at doses of 1 to 28 mM, administered 15 minutes before application of capsaicin, significantly decreased capsaicin-induced scratching movements, conjunctival hyperaemia, eye closure and elevated aqueous protein concentration. These results suggest that for capsaicin-induced pain activity, diltiazem decreases pain and neurogenic inflammation and may be useful as both an analgesic and an anti-inflammatory agent in the eye.

It was also shown that contractile responses to capsaicin were partially inhibited by morphine (5×100 μM) (Zhang et al. (1984) *Exp. Eye Res.*, 38, 153-163). In the same way as in rats, topical application of a drop of morphine sulphate (5 μM) attenuates capsaicin-induced blinking in a concentration-dependent manner. However, morphine has no effect on blinking when applied to healthy, non-inflamed rat cornea. Additionally, the analgesic and anti-inflammatory effects of morphine have been prevented by first administering opioid receptor antagonists such as naloxone, CTAP and naltrindole. Morphine acts on mu- and delta-opioid receptors located in the rat cornea to attenuate inflammation and hyperalgesia (Zhang et al. (2003) *Pain*, 105, 455-65).

1) "Acute" Treatment

A test comparable to that described above was used (Gonzalez et al. (1993) *Invest. Ophthalmol. Vis. Sci.*, 34(12), 3329-3335) to evaluate the compounds of formula (I) of the present invention in New Zealand white rabbits with as positive control a TRPV1 antagonist, capsazepine, instilled at 5 mM (8 animals per group) compared with vehicle alone, 0.9% NaCl (3 animals). The procedure and the timing were as follows:

| Day | Time | Procedure | Eye Examination |
|---|---|---|---|
| — | | General clinical exam, weight | Evaluation of conjunctive hyperaemia Measurement of palpebral opening |
| D0 | 15 min before induction | General clinical exam Administration of the test, control and reference product (50 μL in the right eye for the test and control product and 30 μL in the right eye for the reference product) | Evaluation of conjunctive hyperaemia |
| | Just before induction | — | Evaluation of conjunctive hyperaemia Measurement of palpebral opening |
| | 0 | Induction of ocular pain with capsaicin (30 μL in the right eye) | — |
| | 1 min 5 min 10 min 15 min 20 min 25 min 30 min 40 min 50 min 60 min | — | Evaluation of conjunctive hyperaemia Measurement of palpebral opening |
| | — | | — |

Example 1

Analgesic effect of compound 1 (10 mM) in the model of capsaicin-induced ocular pain (33 mM).

Compound 1

Figure 1:
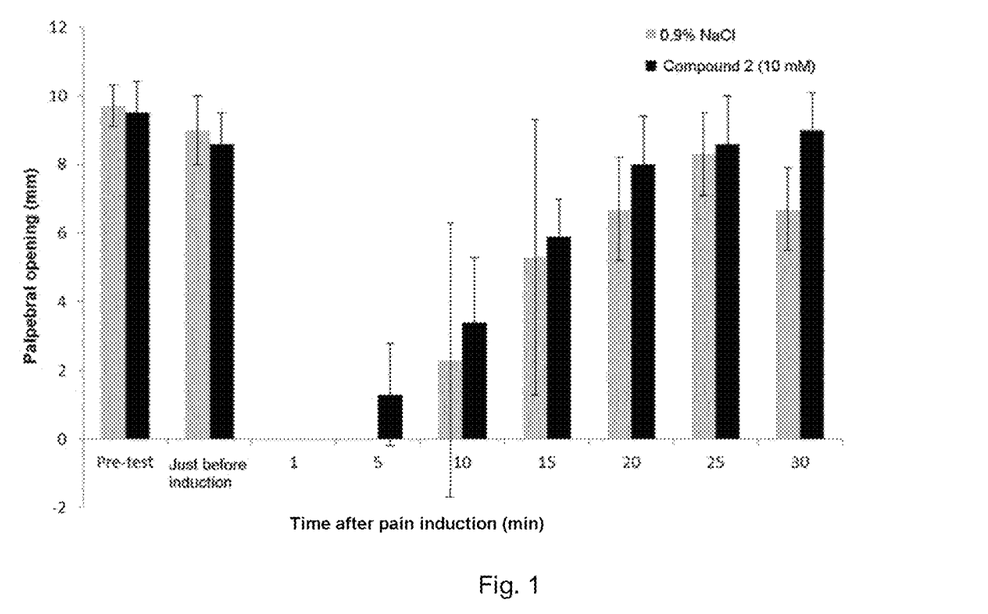
FIG. 1 is a graph corresponding to Example 1.

The results are shown in FIG. 1 representing the degree of palpebral opening, in mm, at the time of the pre-test, just before pain induction and then at 5, 10, 15, 20, 25 and 30 min after pain induction.

Grey histograms: the administered solution contains 0.9% NaCl.

Black histograms: the administered solution contains 10 mM compound 1.

Example 2

Analgesic effect of compound 2 (10 mM) in the model of capsaicin-induced ocular pain (33 mM).

Compound 2

Figure 2:
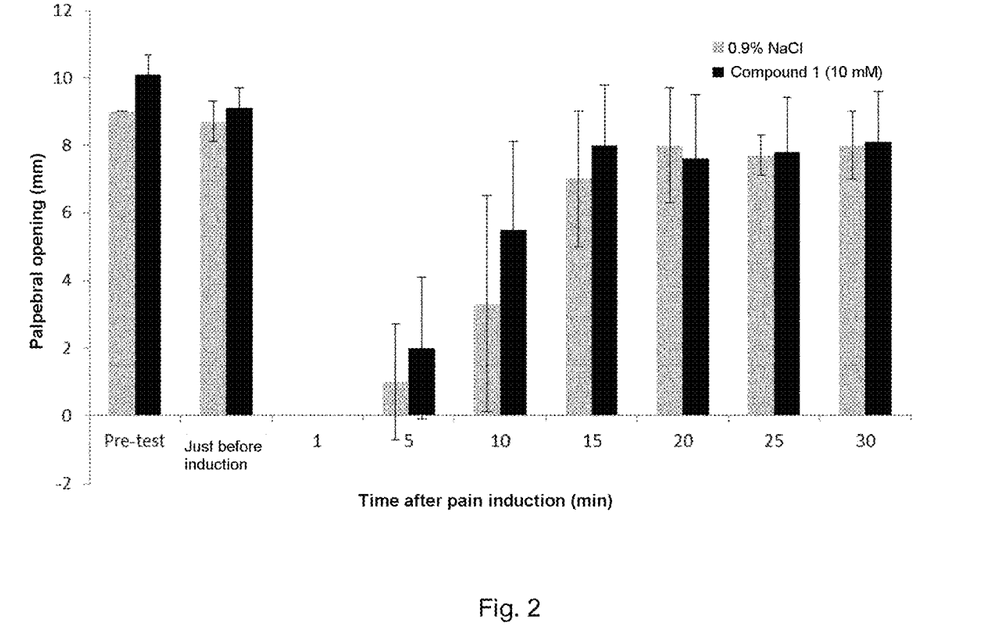
FIG. 2 is a graph corresponding to Example 2.

The results are shown in FIG. 2 representing the degree of palpebral opening, in mm, at the time of the pre-test, just before pain induction and then at 5, 10, 15, 20, 25 and 30 min after pain induction.

Grey histograms: the administered solution contains 0.9% NaCl.

Black histograms: the administered solution contains 10 mM compound 2.

Example 3

Evaluation of corneal pain by observing conjunctival hyperaemia after pain induction (a single instillation of 1% capsaicin (33 mM) in the right eye) in albino rabbits. Pre-treatment with the compound to be tested, 15 min before capsaicin instillation.

Compound 1

Figure 3:
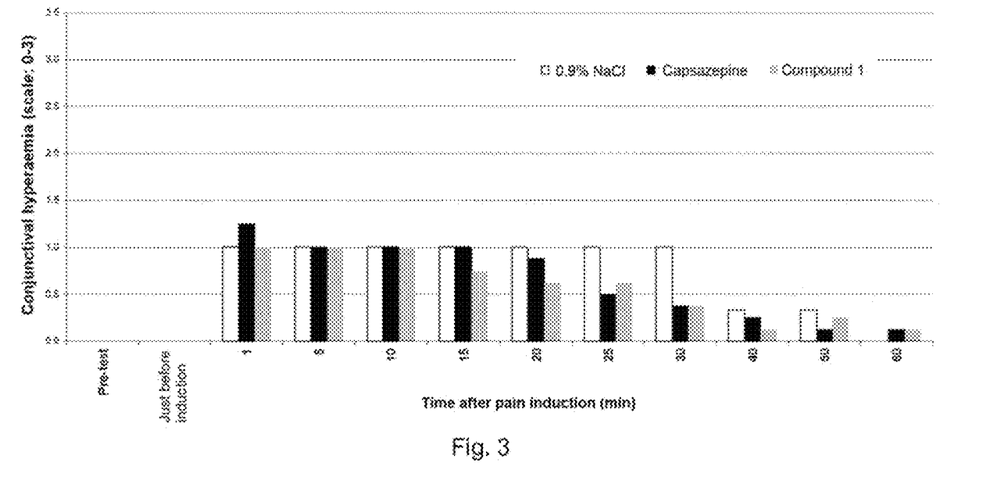
FIG. 3 is a graph corresponding to Example 3.

The results are shown in FIG. 3 representing conjunctival hyperaemia (scale: 0-3) at the time of the pre-test, just before pain induction and then at 1, 5, 10, 15, 20, 25, 30, 40, 50 and 60 min after pain induction.

White histograms: the administered solution contains 0.9% NaCl.

Black histograms: the administered solution contains 5 mM capsazepine (reference control product).

Grey histograms: the administered solution contains 10 mM compound 1.

Example 4

Evaluation of corneal pain by observing conjunctival hyperaemia after pain induction (a single instillation of 1% capsaicin (33 mM) in the right eye) in albino rabbits. Pre-treatment with the compound to be tested, 15 min before capsaicin instillation.

Compound 2

Figure 4:
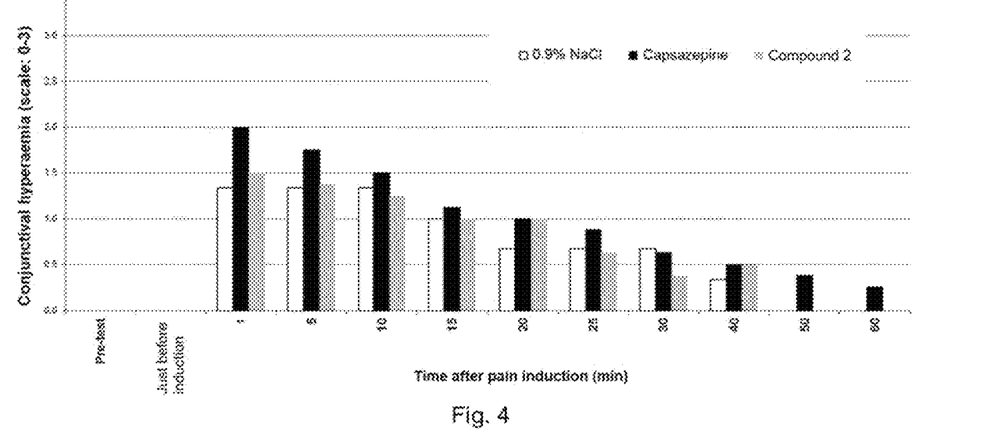
FIG. 4 is a graph corresponding to Example 4.

The results are shown in FIG. 4 representing conjunctival hyperaemia (scale: 0-3) at the time of the pre-test, just before pain induction and then at 1, 5, 10, 15, 20, 25, 30, 40, 50 and 60 min after pain induction.

White histograms: the administered solution contains 0.9% NaCl.

Black histograms: the administered solution contains 5 mM capsazepine (reference control product).

Grey histograms: the administered solution contains 10 mM compound 2.

In our experimental conditions, a single instillation of 10 mM compound 1 or compound 2 showed an analgesic effect following pain induction by capsaicin, on conjunctival hyperaemia and palpebral opening, superior to the reference product, capsazepine.

2) "Chronic" Treatment

The compounds of formula I of the present invention were also tested, in 8-week-old male C57BL/6 mice (JANVIER LABS), using a capsaicin test (100 µM) after twice-daily treatment for 5 days of the compound of formula I on cornea injured beforehand (with a 1.5 mm diameter trephine).

Example 5

Figure 5:
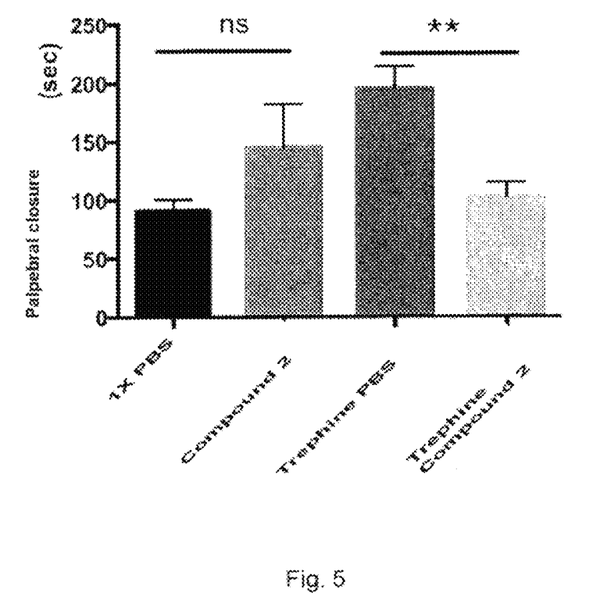
FIG. 5 is a graph corresponding to Example 5.
Figure 6:
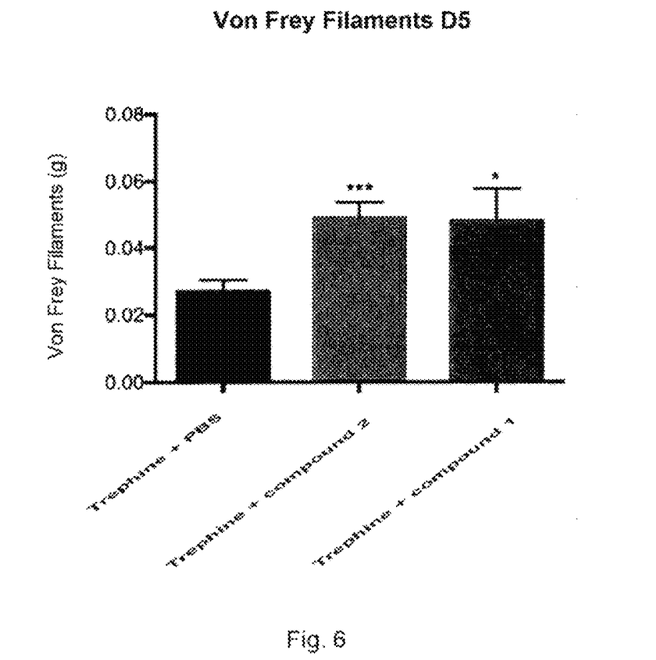
FIG. 6 is a graph corresponding to Example 5 and 6.

Analgesic effect of compound 2 in the model of capsaicin-induced ocular pain (100 µM). A corneal epithelial injury was made on the right cornea of male C57BL/6 mice (JANVIER LABS) using a 1.5 mm diameter trephine. Once the animals were operated on, a twice-daily topical treatment, for 4 days, is carried out with 1×PBS (5 animals per group) or with 10 mM compound 2 (5 animals per group). On day 4, 15 minutes after the last instillation, 100 µM capsaicin is instilled and the behavioural analysis is performed. The results obtained corresponding to the trephine injury alone before capsaicin are shown in FIG. 5 (y-axis: palpebral closure time in seconds). The results obtained after the application of capsaicin are shown in FIG. 6. In these experimental conditions, chronic treatment with 10 mM compound 2 showed a very significant analgesic effect (shorter cumulative palpebral closure time), compared with the control group receiving PBS, following pain induction in the capsaicin test (100 µM).

a) Corneal Injury Using a Trephine in Mice

During this test, de-epithelialization of the corneal epithelium of the left eye of the mouse is carried out using a 1.5 mm diameter trephine. This surgery is carried out under a surgical microscope. This procedure lasts at most 3 minutes per animal. The depth and surface area of corneal de-epithelialization are standardized and then evaluated by a slit-lamp examination. The advantage of this surgical tool is standardization of the injury. The 8-week-old male C57BL/6 mice thus treated receive a twice-daily treatment for 5 days of the compound of formula I or PBS before the application of capsaicin.

Example 6

Additional pain is induced by capsaicin (100 μM). Corneal mechanical sensitivity (allodynia) was measured using Von Frey filaments, 5 days after treatment, on mice treated with compound 1 (10 mM), with compound 2 (10 mM) or, for the control group, with 1×PBS (n=5 animals per group). The results obtained are presented in FIG. 6 (y-axis: weight of the Von Frey filament in grams). The histogram on the left (black) represents the response of mice treated with PBS, the histogram in the middle represents the response of mice treated with compound 1 and the histogram on the right represents the response of mice treated with compound 2. Twice-daily topical treatment for 5 days with compound 1 or compound 2, on a cornea injured beforehand (1.5 mm diameter trephine), induced a significant decrease, when measured with Von Frey filaments, in mechanical sensitivity (expressed as a higher tolerable filament weight) in comparison with the results obtained in control mice treated with 1×PBS (n=5 mice per group).

b) Keratitis Induced by Chronic Instillation of 0.2% Benzalkonium Chloride (BAC)

Chronic instillation of 0.2% benzalkonium chloride induces chronic inflammation of the cornea with generation of ocular pain (Launay et al. (2016) *Neurobiol. Dis.*, 88 16-28). This model was used as a model of chemical keratitis.

Example 7

Figure 7:
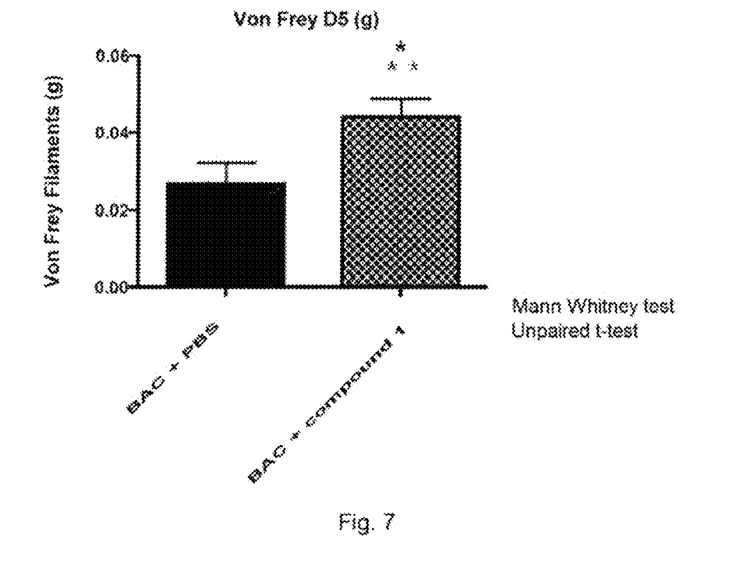
FIG. 7 is a graph corresponding to Example 7.

Study of corneal sensitivity in mice treated twice-daily with compound 2 for 5 days first treated with 0.2% BAC for 6 days. The corneal mechanical sensitivity of male C57BL/6 mice, treated with 0.2% BAC for 6 days, then twice-daily with compound 2 for 5 days, was evaluated at various times using Von Frey filaments, compared with a control group receiving twice-daily 1×PBS (n=10 animals per group). The use of Von Frey filaments (applied to the centre of the cornea of a conscious animal) is perfectly feasible for measuring corneal mechanical allodynia in mice. In the context of dry eye, the technique produces mechanical allodynia in the patient: the simple fact of closing the eyelid induces a painful sensation. Lastly, this behavioural test is most like the one used in human clinical practice (Cochet-Bonnet) to measure corneal mechanical sensitivity.

The results obtained are presented in FIG. 7 (y-axis: weight of the Von Frey filament in grams). The histogram on the left represents the response of mice treated with PBS, while the histogram on the right represents the response of mice treated with compound 2. FIG. 7 shows that mechanical allodynia induced by 0.2% BAC is significantly reduced (higher sensitivity threshold) in the presence of compound 2 (10 mM).

c) Model of Inflammation Induced by Lipopolysaccharide (LPS) in Mice

Bacterial lipopolysaccharide (LPS, endotoxin) is a potent stimulator of inflammatory responses and contributes to microbial keratitis and to corneal ulcers (Khatri et al. 2002 *Invest. Ophthal. Vis. Sci.*, 43 2278-2284).

Example 8

Compound 2

Figure 8:
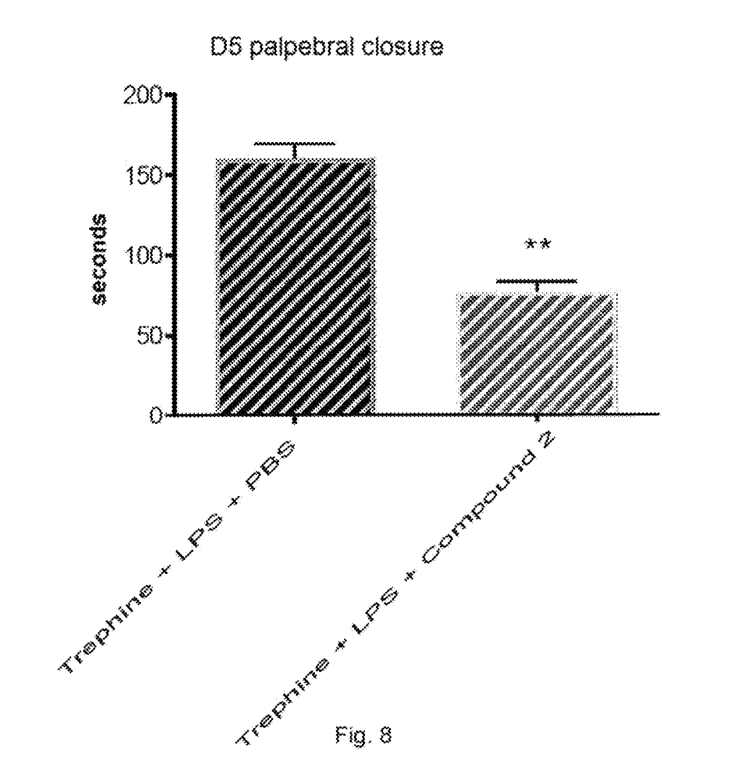
FIG. 8 is a graph corresponding to Example 8.

Effect of compound 2 in a model of LPS-induced inflammation (50 μg). A corneal epithelial injury (scratch) is made with a trephine (1.5 mm diameter) in mice, followed by topical treatment with LPS (50 μg, two administrations on days 1 and 4) then twice-daily chronic treatment for 5 days with 1×PBS (control group) or with compound 2 (10 mM) (n=6 animals per group), followed by capsaicin instillation (100 μM) on day 5. The results obtained are presented in FIG. 8 (y-axis: palpebral closure time in seconds). The histogram on the left represents the response of mice treated with PBS, while the histogram on the right represents the response of mice treated with compound 2. In these experimental conditions of LPS-induced bacterial keratitis, chronic treatment with 10 mM compound 2 thus has a very significant analgesic effect (shorter cumulative palpebral closure time), compared with the control group receiving PBS.

What is claimed is:
1. A method for treating eye pain in a subject in need thereof, the method comprising:
   administering a compound having formula (I) to the subject, the compound having formula (I) being:

$R_1$—NH—CH($R_2$)—P(=O)(OH)—$CH_2$—C($R_3$)
   ($R_4$)—CONH—C($R_5$)($R_6$)—COO$R_7$ wherein:
$R_1$ is:
   a hydrogen, or
   an (acyloxy)alkyl carbamate group —C(=O)—O—C(R)(R')—OC(=O)—R" wherein R and R' are each independently a hydrogen, an alkyl group and R" is an alkyl group;
$R_2$ is:
   a linear or branched, saturated or unsaturated hydrocarbon chain having from 1 to 6 carbon atoms;
$R_3$ and $R_4$ are each independently:
   a hydrogen
   a phenyl or benzyl group, optionally substituted on the phenyl ring by:
      *1 to 5 halogen atoms;
      *an OH, SH, OR" or SR" radical, R" is an alkyl group;
      *an amino group optionally mono- or di-substituted by a cyclic or linear aliphatic group having from 1 to 6 carbon atoms;
      *a trifluoromethyl group;
      *an aromatic or heteroaromatic group having 5 or 6 atoms;
   a heteroaromatic group having 5 or 6 atoms, containing 1 or 2 heteroatom(s) selected from oxygen, nitrogen or sulphur, wherein the sulphur and nitrogen atoms may be oxidized in S-oxide or N-oxide form; or a methylene substituted by an aromatic or saturated heterocycle having 5 or 6 atoms, the heteroatom being an oxygen, a nitrogen or a sulphur, wherein the nitrogen and sulphur atoms may be oxidized in N-oxide or S-oxide form;

$R_3$ and $R_4$ are not simultaneously a hydrogen atom;

$R_5$ and $R_6$ are each independently:
  a hydrogen atom; or
  a linear or branched, saturated or unsaturated hydrocarbon chain having from 1 to 6 carbon atoms; and $R_7$ is:
  a hydrogen;
  a $CH_2COOR'''$ or $CH(CH_3)COOR'''$ radical, R''' being:
    *a saturated hydrocarbon chain having from 1 to 6 carbon atoms, optionally substituted by a $C_1$ to $C_3$ alkoxy group;
    *a $C_5$ to $C_8$ cycloalkyl group;
    *a phenyl, benzyl or alkyl group; or
  a CH(R)O—C(O)OR' or CH(R)OC(O)R' group wherein R and R' are each independently a hydrogen or an alkyl group;

or a pharmaceutically acceptable salt thereof.

2. The method according to claim 1, wherein the eye pain is associated with dry eye syndrome.

3. The method according to claim 1, wherein the eye pain is associated with corneal neuropathic pain.

4. The method according to claim 1, wherein in the compound of formula (I), $R_1$ is an (acyloxy)alkyl carbamate group —C(=O)—O—C(R)(R')—OC(=O)—R''.

5. The method according to claim 1, wherein in the compound of formula (I), $R_1$ is a —C(=O)—O—CHMe—OC(=O)—CHMe$_2$ group.

6. The method according to claim 1, wherein in the compound of formula (I), $R_3$ is a hydrogen atom.

7. The method according to claim 1, wherein in the compound of formula (I), $R_4$ is benzyl group optionally substituted by 1 to 5 halogen atom(s), a phenyl or a 5- or 6-member heteroaromatic group.

8. The method according to claim 7, wherein in the compound of formula (I) $R_4$ is benzyl group optionally substituted by 1 to 5 fluorine or bromine.

9. The method according to claim 1, wherein in the compound of formula (I), $R_5$ is a hydrogen atom.

10. The method according to claim 1, wherein in the compound of formula (I), $R_6$ is an alkyl group.

11. The method according to claim 10, wherein in the compound of formula (I), $R_6$ is a methyl group.

12. The method according to claim 1, wherein in the compound of formula (I), $R_7$ is a hydrogen atom.

13. The method according to claim 1, wherein the compound of formula (I) is selected from the following compounds:

2-(2-Biphenyl-4-ylmethyl-3-{hydroxy-[1-(1-isobutyryloxy-ethoxycarbonylamino)-ethyl]-phosphinoyl}-propionylamino)-propionic acid benzyl ester;

2-(2-Biphenyl-4-ylmethyl-3-{hydroxy-[1-(1-isobutyryloxy-ethoxycarbonylamino)-ethyl]-phosphinoyl}-propionylamino)-propionic acid;

2-(2-Biphenyl-4-ylmethyl-3-{hydroxy-[1-(1-isobutyryloxy-ethoxycarbonylamino)-ethyl]-phosphinoyl}-propionylamino)-propionic acid ethyl ester;

2-(2-Biphenyl-4-ylmethyl-3-{hydroxy-[1-(1-isobutyryloxy-ethoxycarbonylamino)-ethyl]-phosphinoyl}-propionylamino)-propionic acid ethoxycarbonyloxy ester;

2-(2-(4-Bromo-benzyl)-3-{hydroxy-[1-(1-isobutyryloxyethoxycarbonylamino)-ethyl]-phosphinoyl}-propionylamino)-propionic acid benzyl ester;

2-(2-(4-Bromo-benzyl)-3-{hydroxy-[1-(1-isobutyryloxyethoxycarbonylamino)-ethyl]-phosphinoyl}-propionylamino)-propionic acid;

2-(2-Biphenyl-4-ylmethyl-3-{hydroxy-[1-(amino)-ethyl]-phosphinoyl}-propionylamino)-propionic acid benzyl ester;

2-(2-Biphenyl-4-ylmethyl-3-{hydroxy-[1-(amino)-ethyl]-phosphinoyl}-propionylamino)-propionic acid;

2-(2-Biphenyl-4-ylmethyl-3-{hydroxy-[1-(1amino)-ethyl]-phosphinoyl}-propionylamino)-propionic acid ethyl ester;

2-(2-Biphenyl-4-ylmethyl-3-{hydroxy-[1-(amino)-ethyl]-phosphinoyl}-propionylamino)-propionic acid ethoxycarbonyloxy ester;

2-(2-(4-Bromo-benzyl)-3-{hydroxy-[1-(amino)-ethyl]-phosphinoyl}-propionylamino)-propionic acid benzyl ester;

2-(2-(4-Bromo-benzyl)-3-{hydroxy-[1-(amino)-ethyl]-phosphinoyl}-propionylamino)-propionic acid; and 2-(2-(4-Bromo-benzyl)-3-{hydroxy-[1-(amino)-ethyl]-phosphinoyl}-propionylamino)-propionic acid ethyl ester.

14. The method according to claim 1, wherein the compound of formula (I) is formulated as an ophthalmic composition comprising one of: eye drops, ophthalmic ointments, ophthalmic gels, or ophthalmic inserts.

15. The method according to claim 14, wherein the ophthalmic composition comprises from 0.01% to 3% (weight/volume) of the compound of formula (I).

16. The method according to claim 14 wherein the ophthalmic composition is an aqueous solution.

17. The method according to claim 16, wherein the aqueous solution has a pH of from 5.5 to 8.

18. The method according to claim 14, wherein the ophthalmic composition further comprises cyclodextrin or sodium polystyrene sulphonate.

19. The method according to claim 18, wherein the cyclodextrin is hydroxypropyl beta-cyclodextrin or sulphobutyl ether beta-cyclodextrin.

20. The method according to claim 1, wherein in the compound of formula (I) at least one of $R_3$ and $R_4$ is a phenyl or a benzyl group substituted on the phenyl ring by 1 to 5 fluorine or bromine atoms.

* * * * *